United States Patent [19]

Choi

[11] Patent Number: 4,827,007

[45] Date of Patent: May 2, 1989

[54] NOVEL BIS(SILOXANE) DERIVATIVES AND A PROCESS FOR THEIR MANUFACTURE

[75] Inventor: Sam Kwon Choi, Seoul, Rep. of Korea

[73] Assignee: Korea Advanced Institute of Science and Technology, Rep. of Korea

[21] Appl. No.: 245,337

[22] Filed: Sep. 15, 1988

[30] Foreign Application Priority Data

Sep. 26, 1987 [KR] Rep. of Korea ............... 10694/1987

[51] Int. Cl.$^4$ .......................... C07F 7/08; C07F 7/18
[52] U.S. Cl. .................................................. 556/444
[58] Field of Search ........................................ 556/444

[56] References Cited

U.S. PATENT DOCUMENTS 3,254,132 5/1966 Wotil et al. ...................... 556/444 X
4,277,610 7/1981 Cohen .............................. 556/444 X Primary Examiner—Paul F. Shaver
Attorney, Agent, or Firm—Darby & Darby

[57] ABSTRACT

The present invention relates to the preparation of bis(-siloxane) derivatives of the chemical formula(I) which are useful for as an initiator to group transfer polymerization.

The initiators of the formula(I) can be obtained from reacting lithium diisoalkylamide of the formula (III) and diester compounds of the formula(IV) with trialkylchlorosilicon of the formula(V)

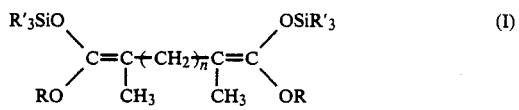

Wherein, R and R' stand for a straight or branched chain of aliphatic hydrocarbons, n is integer of 0–2.

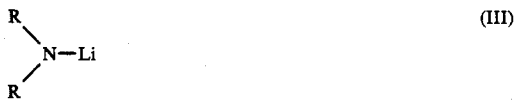

Wherein R is the same as the R in formula(I)

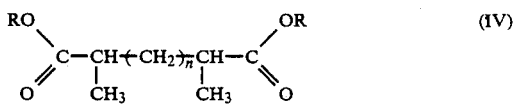

Wherein R and n are the same as the R and n in the formula(I)

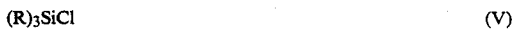

Wherein R stands for methyl or ethyl group.

3 Claims, No Drawings

NOVEL BIS(SILOXANE) DERIVATIVES AND A PROCESS FOR THEIR MANUFACTURE

BACKGROUND OF THE INVENTION

The present invention relates to the preparation of novel bis(siloxane) derivatives of the chemical formula (I) which are useful in particular as an initiator for group transfer polymerization (hereinafter referred to as GTP).

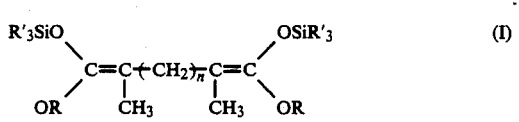  (I)

Wherein R is either a straight or branched chain of aliphatic hydrocarbons, i.e., methyl, ethyl, propyl, isopropyl, butyl, isobutyl, t-butyl, pentyl, 2-methylbutyl, 3-methylbutyl group. Particularly, preferred aliphatic hydrocarbons are $C_{1-4}$, R' is the same as R, n is integer of 0 to 2.

According to some prior arts as Polymer Preprint, Am. Chem. Soc. 27 (1), 161 1986, it discloses that GTP is a fundamentally new method for polymer formation. It involves the repeated addition of monomer to a growing polymer chain end which carries a reactive ketene silyl acetal group. During the addition, the silyl group transfers to incoming monomer regenerating a new ketene acetal function ready for reactive with more monomer, hence the name group transfer polymerization. Moreover, it also discloses that GTP has recently been reported to be a valuable new method for polymerization of $\alpha,\beta$-unsaturated esters, amides, and nitriles using ketene silyl acetals as initiators and certain Lewis acids or anions as catalysts.

As is well known in polymer chemistry, the GTP process is illustrated by Equation 1 for methylmethacrylate monomer (MMA). A catalyst, e.g., a sotuble bifluoride is required for the reaction to proceed. GTP provides "living polymer" rapidly at room temperature and offers new dimensions in the construction and design of polymer chains.

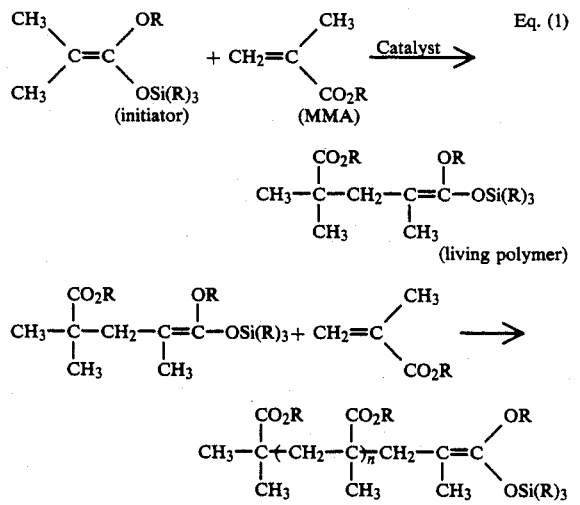

With certain initiators and catalysts, induction periods are noted, for example, with trimethyl silyl cyanide. 1-Alkoxy-1-(trimethylsiloxy)-2-methyl-1-alkenes, eg., Eq. (1) is the most powerful initiators for GTP. Large alkyl groups on the silicon lower the rate of polymerization. The —OR group on the initiator will be on one end of every polymer chain and can be used to introduce functionality. Compounds which can rearrange to ketene acetals such as $\alpha$-silyl esters will also initiate GTP as Equation (2).

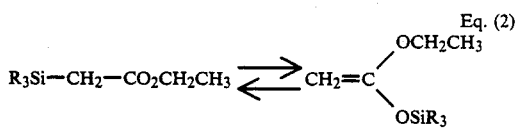

In addition, certain silyl derivatives which add to methacrylate, for example trimethylsilyl cyanide or trimethylsilyl methylsulfide, act as initiators, through generation of ketene acetals as Equation (3). The trimethylsilyl cyanide itself can be generated in situ by reaction of ammonium cyanide ($R_4N^+CN^-$) with trimethylchlorosilicon.

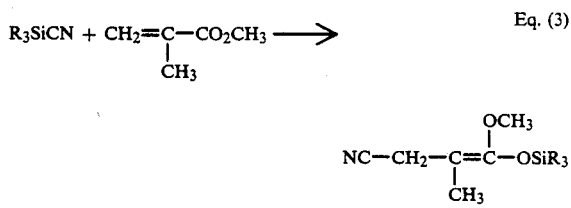

Meanwhile, it is said that a variety of phosphorous terminated polymers can be synthesized by the use of phosphorous-containing ketene silyl acetals prepared by the thermal addition of silyl phosphites to $\alpha,\beta$-unsaturated esters. That is to say, Synthesis 1982, 497 and 1982, 915 disclose the preparation of phosphorous terminated polymers as Equation(4).

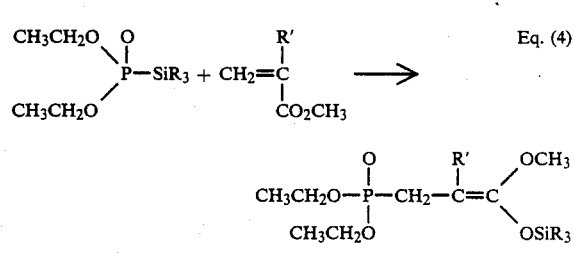

As can be seen in U.S. Pat. Nos. 4,417,034 and 4,508,880, well-known GTP initiators are $\alpha,\beta$-unsaturated ketene silyl acetals. Therefore acrylates, methacrylates, acrytonitriles can be polymerized and/or copolymerized by the use of aforementioned prior initiators.

There are some drawbacks in the prior arts to prepare an ABA type triblock copolymer by the use of the prior initiators. In order to prepare an ABA type triblock copolymer, in the beginning an A monomer alone is polymerized to be occuring a living A polymer which is preferably molecular weight to be wanted and then B monomer is copolymerized with the living A polymer. Finally an ABA triblock copolymer can be obtained by the reaction of an A monomer with the AB two blocks polymer. Therefore the process of the ABA type triblock copolymer in the prior arts is very complicated as the above-captioned description.

SUMMARY OF THE INVENTION

The present invention, relates to the preparation of novel bis(siloxane) derivatives of the chemical formula(I) which are widely useful for as an initiator group transfer polymerization.

Bis(siloxane) derivatives of the formula(I) can be prepared from the reaction product of lithium diisoalkylamide of the formula(III) and diester compounds of the formula(IV) with trialkylchlorosilicon of the formula(V).

Accordingly, it is therefore an object of the present invention to provide preparing novel bis(siloxane)-derivatives which are useful as an initiator for the polymerization of α,β-unsaturated hydrocarbon monomers. The preferred monomers include methacrylate, methylmethacrylate, butylmethacrylate, allylmethacrylate, acrylonitrile.

DETAILED DESCRIPTION OF THE INVENTION

The inventor has been approaching to overcome the technical and economical problems of prior initiators and has been surprisingly found novel GTP initiators.

The GTP initiators of the present invention are bis (siloxane) derivatives of the formula(I) which are essentially comprising silyl acetals in each side of the aliphatic dialkene.

As can be seen under-mentioned chemical route, the GTP initiators of the present invention having difunctional groups can be easily obtained from the chemical background of Macromolecules, 20(7) 1473(1987). More specifically to say, lithium diisoalkylamides of the formula(III) which are starting material of the invention can be synthesized by the reaction of secondary amines of the formula(II) with butyllithium in the presence of THF and under nitrogen gas. And the reaction mixture is kept to below freezing point.

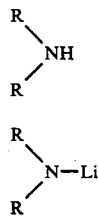

In the formulae(II) and (III), R is aliphatic alkyl group such as ethyl, propyl, isopropyl, n-butyl, isobutyl and t-butyl.

Diester of the formula(IV) and trialkylchlorosilicon of the formula(V) are added into the solution of lithium diisoalkylamide of the formula(III) with stirring. Finally bis (siloxane) derivatives of the formula(I) can be obtained when the reaction mixture of the compound is raised to reach at room temperature.

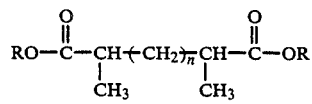

Wherein in the formula(IV), R and n are the same as the R and n in the compound of the formula(I). In the formula (V) R represents methyl or ethyl group.

The following examples further illustrate the present invention, but they are not constructed to limit the scope of the invention.

Example 1

The method for the preparation of [1,6-dimethoxy-2,5-dimethyl-1,5-hexadien-1,6-diyl bis(oxy)] bis(trimethylsilane)

0.2 mol of diisopropylamine and 150 ml of tetrahydrofuran were added to a 100 ml, three necks, round bottom flask charged with nitrogen gas and then the solution was cooled to $-30°$ C. Lithium diisobutyl amide was obtained while 2.5 mol of n-butyllithium was added to the solution with stirring. After cooling lithium diisobutylamide at around $-90°$ C., 0.1 mol of dimethyl-2,5-dimethyladipate and 0.5 mol of trimethylchlorosilane were added slowly and raised temperature to reach at $25°$ C., and then the lithium chloride in the solution was filtered off.

Evaporation in vacuo (0.1 mmHg, $84°$ C.) of the filtrate to dryness gave the subject initiator (yield: 30%). bp $87°$-$88°$ C. (0.1 Torr)

H-NMR (CDcl₃) (ppm): 0.2(s, 18H), 1.6(s, 6H), 2.0(s, 4H), 3.7(s, 6H).

$^{13}$C-NMR(CDCl₃)(ppm): 0(1), 15(5), 30(4), 57(2), 96(3), 150(6).

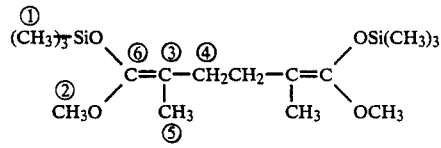

EXAMPLE 2

The method for the preparation of [1,6-dimethoxy-2,5-dimethyl-1,5-hexadien-1,6-diyl bis(oxy)] bis(trimethylsilane)

Lithium diisopropylamide prepared from diisopropylamine (0.2 mol) and n-butyllithium (0.2 mol) at $-30°$ C. was added dropwise to the mixture of dimethyl-2,5-dimethyladipate (20.2 g, 0.1 mol) and chlorotrimethylsilane (50 ml, 0.5 mol) in tetrahydrofuran at $-78°$ C. After the mixture was stirred for 30 mim, it was filtered and the solvent was evaporated. Then the residue was fractionally distilled under redused pressure to give 24.5 g of the subject initiator(yield 70%).

EXAMPLE 3

The method for the preparation of [1,5-dimethoxy-2,4-dimethyl-1,4-pentadien-1,5-diyl bis(oxy)] bis(trimethylsilane)

The procedure of Example 1 was repeated, except that dimethyl-2,4-dimethylglutamate was used in place of dimethyl-2,5-dimethyladipate, to obtain the subject initiator.

$^1$H-NMR(CDCl₃)(ppm): 0.6(s, 18H), 1.9(s, 6H), 3.0(s, 2H), 4.0(s, 6H).

$^{13}$C-NMR(CDCl₃)(ppm): 0(1), 13(5), 31(4), 57(2), 94(3), 151(6).

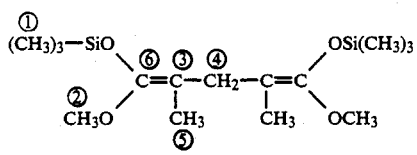

EXAMPLE 4

The method for the preparation of [1,4-dimethoxy-2,3-dimethyl-1,3-butadien-1,4-diyl bis(oxy)] bis(trimethylsilane)

After cooling the lithium diisobutylamide obtained from Example 1 at a temperature of −75° C., 0.1 mol dimethyl-2,4-dimethylsuccinate and 0.5 mol of trimethyl-chlorosilane were added slowly and raised temperature to reach at 30° C. and filtered. The filtrate was distilled under vacuo(0.1 mmHg, 84° C.) to give the subject initiator (yield 75%).

$^1$H-NMR(CDCl$_3$, δ): 0.2(s, 18H, (CH$_3$)$_3$Si—), 1.7(s, 6H, CH$_3$—), 3.6(s, 6H, —OCH$_3$).

$^{13}$C-NMR(CDCl$_3$)(ppm): 150(1), 97(2), 58(3), 30(4), 0(5).

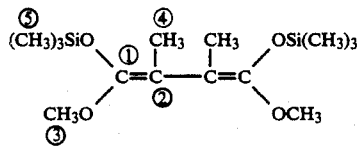

What is claimed is:

1. Bis(siloxane) derivatives represented by the following general formula(I)

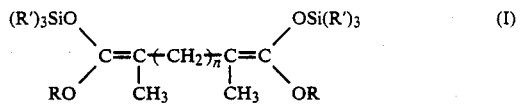

wherein R and R' are methyl, ethyl, propyl, isopropyl, n-butyl, isobutyl, t-butyl, pentyl, 2-methylbutyl, 3-methylbutyl, n is integer of 0-2.

2. A process for the manufacture of bis(siloxane) derivatives of the formula(I) are manufactured by the reaction of lithium diisoalkylamide of the formula(III) and diester compounds of the formula(IV) with trialkylchlorosilicon of the formula(V)

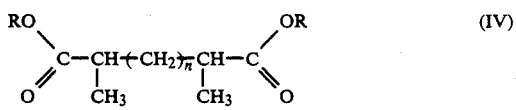

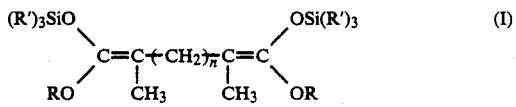

wherein in the formula(I), (III) and (IV), R and R' are methyl, ethyl, propyl, isopropyl, n-butyl, isobutyl, t-butyl, pentyl, 2-methylbutyl, 3-methylbutyl; in the formula(V), R' is selected from among methyl or ethyl; in the formulae(I) and (IV), n is integer of 0-2.

3. The process of claim 2, wherein the reaction temperature is carried out at the temperature of −90° C. to 40° C.

* * * * *